United States Patent [19]

Palinczar et al.

[11] 4,339,550

[45] Jul. 13, 1982

[54] FOAM PRODUCTS

[75] Inventors: Victor Palinczar, Trenton; Thomas F. Santini, Allentown, both of N.J.

[73] Assignee: Carter-Wallace, Inc., New York, N.Y.

[21] Appl. No.: 228,069

[22] Filed: Jan. 26, 1981

[51] Int. Cl.³ ............................................. C08G 18/14
[52] U.S. Cl. ........................................ 521/99; 424/76; 521/107; 521/113; 521/114; 521/116; 521/117; 521/121; 521/128; 521/130; 521/131; 521/159
[58] Field of Search ................. 521/99, 107, 113, 114, 521/116, 117, 121, 128, 130, 131, 159; 424/76

[56] References Cited

U.S. PATENT DOCUMENTS

| | | | |
|---|---|---|---|
| 3,034,996 | 5/1962 | Kaplan | 521/107 |
| 3,127,312 | 3/1964 | Boyer | 521/113 |
| 4,156,067 | 5/1979 | Gould | 424/76 |
| 4,226,944 | 10/1980 | Stone et al. | 521/76 |

*Primary Examiner*—Maurice J. Welsh
*Attorney, Agent, or Firm*—Kevin B. Clarke

[57] ABSTRACT

Foam products are disclosed which are produced by incorporating active materials, utilizing in situ methods, into the cell structure of hydrophillic polyurethane foams. The products obtained are characterized by a controlled rate of release of the active material from the foam structure.

9 Claims, No Drawings

FOAM PRODUCTS

This invention relates to novel foam products. In particular this invention relates to novel hydrophillic foam products prepared by using "in-situ" impregnation techniques to incorporate active substances. More particularly this invention relates to the incorporation of volatile materials into hydrophillic polyurethane foam structures for the purpose of achieving a sustained, controlled release of the volatile materials from the foam structure.

It has been known for a long time past, i.e., U.S. Pat. No. 2,661,238, and U.K. Pat. No. 1,544,221 now to impregnate articles, having a high degree of porosity, with materials, preferably in the form of liquids, that will evaporate slowly at normal temperatures and pressures and thus permeate the adjacent atmosphere. Further, various sustained release means comprising a polymeric carrier have been proposed, i.e., U.S. Pat. Nos. 3,857,932; 3,975,350; 4,202,880; U.K. Pat. No. 1,135,066 and German patent specification No. 2,528,068. Among the materials that may be impregnated into porous materials have been medicaments, perfumes, deodorants, germicides, pesticides, disinfecting and sterlizing agents, etc.

A substantial market has developed over the past few years in environmental deodorant products such as air fresheners. The currently marketed products generally consist of having the volatile material incorporated into or onto various types of substrates such as wicks, gels, blotters, plaster and waxes. The rate at which the volatile material is dispersed into the surrounding environs is generally controlled by increasing or decreasing the area of coated or impregnated substrate exposed to the atmosphere.

The early years of industrial/consumer foams saw the development of what are termed "in-situ" foam impregnation techniques. These techniques allow for the addition of specific ingredients to the foam during the production or foaming process. The most widely known products utilizing these techniques are the slow release room deodorizers. As the foam ingredients are mixed, a special flavor or fragrance is added in specific quantities.

"In-situ" techniques using presently available polyurethane systems, while providing the marketplace with new products, have several advantages but also numerous limitations. Among the advantages is low cost since additives can be put into the foam during the initial production operation. Also the amount of the additive can be carefully controlled. Further, the size of the foam is not a limiting factor and the additives can be proportioned equally throughout this product.

Limitations of the "in-situ" techniques using previously available polyurethane foam systems include the limited amount of ingredients that can be added to the initial foam mix and the limited variety of these ingredients that can be added to the initial foam mix. Most importantly, many of the prior art polyurethane foaming systems are exothermic reactions which cause insurmountable or impractical heat problems or adverse reactions. This is especially true for delicate and sensitive volatile additives such as flavors and fragrances. In accordance with the present invention we have found that by using a hydrophillic polyurethane polymer, the adverse effects produced by exothermic reactions are eliminated, and the variety of ingredients that can be incorporated into the system of this present invention are practically unlimited.

We have also found that by using a hydrophillic polyurethane polymer, the incorporation of sensitive volatile materials into foam for the express purpose of achieving a sustained release of the volatile materials from the foam can be achieved. In accordance with the methods of the present invention, the sensitive volatile substance may become an intricate part of the foam structure by means of a chemical reaction and is irreversible. Where the volatile materials do not become an intricate part of the foam structure by means of a chemical reaction, sustained release of volatile materials can be accomplished by means of controlling the pore size of the polyurethane foam structure. Sustained release is further accomplished by physical means as a result of the hydrophillic polyurethane polymer's propensity to be compatible with a wide range of "control release ingredients", that aid in producing a sustained release effect. The use of these ingredients in combination with the hydrophillic polyurethane polymer is another aspect of the present invention. The present invention is a significant advance over the simple incorporation of a volatile substance into a foam after formation of the foam.

The technology utilized for the purpose of this invention involves an "in-situ" method of incorporating the volatile material and other "control release" ingredients, when necessary, in order to produce an additive capable of sustained release prior to the formation of the polyurethane foam. Once foaming has been completed the volatile materials and other essential ingredients are distributed evenly throughout the foam matrix with their fugitive nature held in check by the cellular structure of the foam.

A broad spectrum of volatile ingredients and essential ingredients can be incorporated into foams in accordance with the present invention, limited only by their lack of compatibility with the components used in the preparation of the foams and the reaction conditions employed. In general ingredients that are released, such as decongestants, perfumes, deodorants, germicides, insecticide agents, etc., which are referred to as volatile materials in this specification, are often non-polar in nature and therefore have a tendency to be soluble in the hydrophillic polyurethane polymer. There is a limiting factor however to the extent of their use since they have the ability to reduce the foaming capacity of the polymer. This effect, reduction of foaming capacity, becomes more pronounced with the addition of specific types of "control release" ingredients, usually non polar in nature, that are employed to increase the degree of sustained release. The situation becomes even more complexed with this present system because the polymer is admixed with large amounts of an aqueous reactant. The aqueous reactant has a tendency to decrease the level of volatile materials and specific types of "control release" ingredients that can be incorporated into this system by lowering their solubility.

The present invention provides for methods which lessen the inherent difficulties encountered by ingredients that either decrease the foaming ability of the polymer and/or influence solubility. These methods make use of surface active agents, which in turn satisfy the overall hydrophillic/lipophillic balance of the system. The use of preferred surface active agents which satisfy the overall HLB of the system can also play additional roles in that their use may: (1) contribute in the sustained release control by the nature of their chemical design, and (2) control the formation of the pore size of the foam structure.

For purposes of illustrating the present invention, volatile fragrances are incorporated into cellular structures which are useful as air fresheners.

In a preferred embodiment of the present invention a fragrance is incorporated by an in-situ method into a hydrophillic polyurethane foam. However, it should be noted that this does not exclude hydrophobic polyisocyanate-polyol foams from being within the scope of the present invention.

The preferred hydrophillic polyurethane foams employed in the present invention are prepared from a capped polyoxyethylene polyol reactant, having a defined average reaction functionally greater than two, which is mixed with an aqueous reactant. The foams thus generated are characterized by a cross-linked non-linear, molecular network.

The polyoxyethylene polyols used in the preparation of the capped product to be foamed in accordance with the present invention have an average molecular weight of from about 200 to about 20,000 preferably between about 600 and about 6,000 with a hydroxyl functionality of 2 or greater preferably from about 2 to about 8.

The polyoxyethylene polyol is capped by reaction with a polyisocyanate. The capping reaction can be carried out in an inert moisture-free atmosphere, such as under a nitrogen blanket, at atmospheric pressure at a temperature in the range of from about 0° C. to about 120° C. for a period of time ranging up to about 20 hours, depending upon the temperature and the degree to which the reaction mixture is agitated. The capping reaction can also be carried out under ambient conditions so long as the product is not exposed to excess moisture.

The capping is effected using stoichiometric amounts of reactants. It is desirable, however, to use an excess of polyisocyanate in order to insure complete capping of the polyol. The ratio of isocyanate groups to hydroxyl groups is generally between about 1 to about 4 isocyanate groups per hydroxyl group.

The polyisocyanates employed in the capping reaction include PAPI (a polyaryl polymethylene polyisocyanate as defined in U.S. Pat. No. 2,683,730), benzene 1,3,5-triisocyanate; chlorophenyl diisocyanate; diphenyl-2,4,4'-triisocyanate; diphenylmethane-4,4' diisocyanate; 3,3'-dimethoxy-4,4'-biphenylene-diisocanate; 3,3'-dimethyl-4,4'-biphenylene diisocyanate; dicyclohexylmethane-4,4'-diisocyanate; ethylene diisocyanate; 1,6-hexamethylene diisocyanate; isophorone diisocyanate; 4,4'-methylene-diortho-tolylisocyanate; 4,4'-methylene-bis-(phenylisocyanate); naphthalene-1,5-diisocyanate; tolylene diisocyanate; triphenylmethane-4,4',4"-triisocyanate; toluene-2,4,6-triisocyanate; 2,2',5,5'-tetramethyl-4,4'-biphenylene diisocyanate; 2,2',4-trimethyl-1,6-hexane diisocyanate; trimethylenediisocyanate; 4,4'-sulfonylbis (phenylisocyante); xylene diisocyanate; xylene-alphia; 3,3'-dimethyl-4,4'-biphenylene diisocyanate, and the like.

Generally speaking, the readily available aromatic diisocyanates, aliphatic and cycloaliphatic diisocyanates and polyisocyanates or mixtures thereof, having a high degree of reactivity, are suitable for use in the capping reaction.

The preparation of the prepolymers, isocyanate-capped polyoxyethylene polyol reaction products, employed in the present invention may follow any one of several methods such as set out in U.S. Pat. No. 4,137,200.

Blends or mixtures of various polyols and isocyanates may be used as desired so long as the total average isocyanate functionality of the final prepolymer is greater than 2.

One method of preparing the prepolymer is by reacting polyoxyethylene glycol having a reactive functionality equal to 2 with a molar excess of a diisocyanate which leads to an isocyanate-capped polyurethane intermediate product having an isocyanate functionality of 2. Similarly, a polyol such as pentaerythritol having a reactive functionality equal to 4 is reacted with a large excess of a diisocyanate to form an isocyanate-capped polyurethane intermediate having an isocyanate functionality of 2 with the intermediate having an isocyanate functionality of 4, in various molar proportions; the resulting mixtures have an average isocyanate functionality of at least 2 and on treatment with aqueous reactants in the presence of a volatile material will lead to the novel structures of the present invention. Additionally, other monomeric or polymeric polyisocyanate crosslinking agents may be substituted for the isocyanates employed; thus use for instance of tolylene-2,4,6-triisocyanate having a reactive functionality of 3 is an example of a simple monomeric triisocyanate which may be usefully employed to achieve the same objective of imparting to the system an average isocyanate functionality greater than 2.

Another method of preparing the prepolymer is to blend a generally linear polyol with a polyol having at least 3 and preferably from 3 to 8 hydroxyl groups (e.g., trimethylolpropane, trimethylolethane, glycerol, pentaerythritol or sucrose). Generally, polyols having 3 to 4 hydroxyl groups per mole are employed. The polyol blend is then reacted with a sufficient excess of polyisocyanate so that the resulting prepolymer is substantially void of unreacted hydroxyl groups. The excess of polyisocyanate may be present to the extent of 4 isocyanate groups for each hydroxyl group. In carrying out the reaction, it is preferable to initially combine an amount of polyisocyanate which is less than that theoretically required with all the hydroxyl groups of the polyol blend. After allowing the initial reaction to go to substantial completion, a subsequent addition of polyisocyanate can be made so as to bring the amount of polyisocyanate up to theoretical or preferably slightly above, i.e., 5% to 15% above theoretical. The polyols used in this invention are well known water soluble reaction products of the polymerization of ethylene oxide in the presence of a polyfunctional starter compound such as water, ethylene glycol, glycerol, pentaerythritol, sucrose and the like. The molecular weights may be varied over a wide range by adjusting the relative ratios of ethylene oxide monomer to starter compound. The preferred molecular weight ranges from 600 to about 6,000.

Example 1, which follows, demonstrates the technique followed in the preparation of a prepolymer for use in manufacturing the foam structures of the present invention.

EXAMPLE 1

A prepolymer is prepared by admixing 2 molar equivalents of polyethylene glycol having an average molecular weight of 1,000 and 1 molar equivalent of trimethylolpropane. The mixture is dried at 100°–110° C. under a pressure of 5–15 Torr to remove water. The resulting dried mixture is slowly added over a period of about one hour to a vessel containing 6.65 molar equivalents of toluene diisocyanate while stirring the mixture. The temperature is maintained at 60° C. with stirring for three additional hours. Then an additional 1.05 molar equivalents of toluene diisocyanate is added with stirring over a period of about one hour while maintaining the temperature at 60° C. The final reaction mixture contains a 10% molar excess of toluene diisocyanate. All hydroxyl groups are capped with isocyanate and some chain extension occurs because of crosslinking of the polyols with the diisocyanate.

For purposes of illustrating the present invention suitable volatile ingredients which are incorporated into cellular structure of the foam are organic compounds having: (a) a vapor pressure greater than about 10 mm. of mercury at 160° C.; (b) a melting point at atmospheric pressure not higher than 200° C.; (c) a dielectric constant not greater than 30, and preferably less than 10, and (d) a specific gravity at 21° C. between 0.6 and 1.7 and preferably between 0.7 and 1.2. Examples of such volatile ingredients are hydrocarbon oils such as hexane; alcohols such as nerol and 2,6-nonadien-1-Ol; aldehydes such as benzaldehyde and 2-octenal; esters such as methyl salicylate and p-tertiary-butyl cyclohoxyl acetate; ethers such as eugenol methyl ether and yara yara; ketones such as camphor and ionone, acids such as cinnamic and phenylacetic acid; nitro compounds such as benzopyrrole and 2,6-dinitro-3-methoxy-4-tertiary butyl toluene, sulfur compounds such as allylisothiocyanate; phosphate compounds such as 2,2 dichlorovinyl dimethyl phosphate.

Any conventional surface active agent or mixture of surface active agents may be used that produce the desired hydrophillic/lipophilic balance to effect; (a) the incorporation of volatile materials either by themselves or in combination with the essential ingredients used in this invention; (b) the formation of the proper pore size of the foam's cellular structure; and (c) the substained release of the volatile materials. The surface active agents used in this invention are generally, but not limited to, nonionic types. Examples of materials that may be used as a surface active agent component either alone or in admixture are ethers such as: polyoxethylene (20) isohexadecyl ether (Arasolve 200); ether alcohols such as: polyoxyethylene (9) nonyl phenyl ether (Igepal CO 630); ether polyols such as: polyoxyethylene-polyoxypropylene black copolymer (Pluronic L-64); esters such as: polyoxyethylene (40) stearate (MYRJ 52) and polyoxyethylene (2) sorbitan monooleate (Tween 80). Also, the surface active agent should not react with the polyurethane polymer or any constituent of the foam formulation to create difficulties while the foam formation is taking place or deleteriously affect the desired activities when used or while being stored.

Suitable "control release" ingredients for use in controlling the rate of release of the volatile ingredients are materials classified as co-solvents such as polyols represented by propylene glycol and glycerin; polyoxyethylenes represented by the carbowaxes; ethers such as diethylene glycol monomethyl ether, esters such as carbitol acetate, ketones such as diacetone alcohol, and polyaklylene glycols such as UCON 50-HB-260; materials listed as resins such as polyvinyl alcohol, carboxy vinyl polymers (Carbopol 934) hydroxyethyl methacrylate and ethylene oxide polymers (Polyoxes); materials classified as gums such as hydroxpropylmethyl-cellulose, sodium carboxymethyl-cellulose and Karaya gum; materials classified as adsorptive agents such as activated alumina, activated charcoal, corn starch, silicon dioxide and diatomaceous earth, and material classified as absorptive agents such as paraffin low density polyethylene and polyethylene fiber.

The volatile material should be in an amount sufficient to impart the desired activity when exposed to the selected environment. In general, the volatile material is in an amount from about 0.1 to 25% by weight of the total composition, preferably 5 to 10%.

The hydrophillic polyurethane polymer should be in an amount to provide a stable structure for containing the desired additives. In general, the hydrophillic polyurethane polymer is in an amount from 5 to 85% by weight of the total composition, preferably 10 to 60%.

The surface active agent should be added in an amount sufficient to provide the formation of the desired foam pore size and to effectively satisfy the overall HLB of the system. In general, the surface active agents are present in an amount of from 1 to 40% by weight of the total composition, preferably 5 to 20%.

The "control release" ingredient should be present in an amount sufficient to provide the desired controllable release of the volatile materials. In general, the essential ingredients are in an amount from 5 to 80% by weight of the total composition, preferably 20 to 50%.

Water or any other compound which activates the hydrophillic polyurethane polymer to form a stable foam that can also function as a heat sink is also present in an amount from about 5 to 75% by weight of the total composition, preferably 10 to 50%.

To effect foaming and the preparation of the novel impregnated foam structure of the present invention, the capped prepolymer is simply combined with a particular aqueous component. In the case of the present invention, the aqueous component may appear as a water solution having water soluble active materials dissolved therein or insoluble active ingredients may be dispersed therein in such a matter so as to maintain their homogeneity until the foam becomes self contained. Further, active ingredients can also be combined with the prepolymer or with the mixture of prepolymer and water.

In accordance with the present invention, the foamed structure formed by the reaction of the prepolymer and water is impregnated in situ with an active volatile material, preferably in the form of a liquid, that will evaporate slowly from the foam structure at normal ambient conditions and thus permeate the surrounding atmosphere. The active volatile material may be a decongestant, a fragrance, a pesticide, a germicide or a disinfecting agent.

The following examples will aid in demonstrating the present invention. In all cases, unless otherwise noted, all parts and percentages are by weight.

EXAMPLE 2

An air freshener foam is prepared as follows: 25 g. of isocyanate-capped polyoxyethylene polyol is combined with 75 g. of an aqueous reactant mixture. The aqueous reactant mixture is comprised of 28 g. of water, 20 g. of alumina, 7 g. of volatile fragrance, 7 g. of Carobwax 1540, 1.5 g. of Arlasolve 200, 1.5 g. of Pluronic L-64, 8 g. of dipropylene glycol, 1 g. of polyethylene fiber, and 1 g. of stabilizers. The polyoxyethylene polyol and aqueous reactant are mixed together with high shear to obtain a homogenous mixture. Immediately after homogenity is obtained the mixture is poured into a suitable container or casted. The resultant foam is cured in about 10 minutes at ambient conditions.

EXAMPLE 3

An air freshener foam is prepared as follows: 25 g. of isocyanate-capped polyoxyethylene polyol is mixed with 7 g. of volatile fragrance until a complete solution is formed. This solution is combined with 68 g. of an aqueous reactant mixture. The aqueous reactant mixture is comprised of 28 g. of water, 20 g. of Celite (diatomaceous silica), 10 g. of Igepal CO 530, 8 g. dipropylene glycol, 1 g. of short fiber polyethylene and 1 g. of stabilizers. The polyol/fragrance solution and aqueous reactant are then mixed together under high shear to obtain a homogenous mixture. Immediately after homogenity is obtained the mixture is poured into a suitable container or casted. The resultant foam is cured at ambient conditions in about 10 minutes.

EXAMPLE 4

A deodorizing foam to be used in refrigerators, dish washers or other like containers where food contact may exist is prepared as follows: 30 g. of isocyanate-capped polyoxyethylene polyol is combined with 70 g. of an aqueous reactant. The aqueous reactant mixture is comprised of 25 g. of water, 7 g. of natural lemon oil, 8 g. of Igepal CO 530, 20 g. of alumina, 8 g. of dipropylene glycol, 1 g. of polyethylene fiber and 1 g. of stabilizers. The procedure used in Example 2 is suitable for preparing this product.

EXAMPLE 5

A deodorizing absorbent foam is prepared as follows: 25 g. of isocyanate-capped polyoxyethylene polyol is combined with 75 g. of an aqueous reactant, and a volatile material phase. The aqueous reactant mixture is comprised of 28 g. of water, 20 g. of activated charcoal, 8 g. of dipropylene glycol, 10 g. of Igepal CO 530, and 1 g. of stabilizers. The volatile material phase consists of 8 g. of natural lemon oil and 1 g. of polyethylene fiber. The volatile phase and the aqueous reactant are combined together and mixed with the polyol under high shear. Immediately after homogenity is obtained the mixture is poured into a suitable container or casted. The resultant foam is cured at ambient conditions in about 10 minutes.

EXAMPLE 6

A decongestant foam is prepared as follows: 25 g. of isocyanate-capped polyoxethylene polyol is combined with 75 g. of an aqueous reactant. The aqueous reactant mixture is comprised of 25 g. of water, 20 g. of alumina, 4 g. of menthol, 2 g. of camphor, 1.5 g. of methyl salicylate, 2.5 g. of eucalyptol, 8 g. of diprophylene glycol, 10 g. of Igepal CO 530, 1 g. of polyethylene fiber and 1 g. of stabilizer. The process for foamed product is prepared following the procedure of Example 2.

EXAMPLE 7

A disinfectant foam and the like are prepared as follows: 25 g. of isocyanate-capped polyoxethylene polyol is combined with 75 g. of an aqueous reactant mixture. The aqueous reactant mixture is comprised of 30 g. water, 20 g. of alumina, 10 g. of dipropylene glycol, 5 g. of phenol, 8 g. of Igepal CO 530, 1 g. of polyethylene fiber and 1 g. of stabilizers. The foam product is prepared following Example 2.

EXAMPLE 8

An insecticide foam is prepared as follows: 25 g. of isocyanate-capped polyoxethylene polyol is combined with 75 g. of an aqueous reactant mixture. The aqueous reactant mixture is comprised of 28 g. of water, 20 g. of alumina, 8 g. of dipropylene glycol, 7 g. of Vapona, 10 g. of Igepal CO 530, 1 g. of polyethylene fiber and 1 g. of stabilizers. The foam product is prepared as in Example 2.

EXAMPLE 9

A flea collar foam and the like are prepared as follows: 25 g. of isocyanate-capped polyoxethylene polyol is combined with 75 g. of an aqueous reactant mixture. The aqueous reactant mixture is comprised of 30 g. of water, 10 g. of alumina, 10 g. of dipropylene glycol, 5 g. of Carbaryl (Union Carbide's—1-naphthyl-N-methyl carbamate), 8 g. of Igepal CO 530, 1 g. of polyethylene fiber and 1 g. of stabilizers. The foam product is prepared as in Example 2.

EXAMPLE 10

A breath/flavored foam and the like are prepared as follows: 25 g. of isocyanate capped polyoxethylene polyol is combined with 75 g. of an aqueous reactant mixture. The aqueous reactant mixture is comprised of 28 g. of water, 10 g. of alumina, 10 g. of dipropylene glycol, 7 g. of peppermint oil, 8 g. of Igepal CO 530, 1 g. of polyethylene fiber, and 1 g. of stabilizers. The product is prepared as stated in Example 2.

Having thus described the invention with reference to the particular forms thereof, it will be obvious to those skilled in the art to which this invention pertains, that changes and modifications may be made without departing from the spirit and scope of the invention as defined by the appended claims.

What is claimed is:

1. Hydrophilic foam compositions characterized by a cross-linked, non-linear molecular network comprising the "in situ" reaction product of:
    a. a capped polyoxyethylene polyol having a defined isocyanate functionality of from about 2 to about 8 and which is present in the composition in an amount of from about 5% to about 85% by weight of the total composition;
    b. water which is present in an amount of from about 5% to about 75% by weight of the total composition; and
    c. from about 0.1% to about 25% by weight of the total composition of a chemically compatible, essentially non-polar volatile organic compound.

2. The foam composition of claim 1 including a surface active agent or mixtures thereof.

3. A foam composition of claim 1 including a compound selected from the group consisting of from about 5% to about 80% by weight of the total composition of adsorptive agents, absorptive agents, gums, resins, esters, ethers, oxyethylene polymers and mixtures thereof.

4. The foam composition of claim 2 wherein said surface active agent is nonionic and is present in an amount of from about 5% to about 80% by weight of the total composition.

5. The process for incorporating a volatile substance into hydrophilic foam structures for the purpose of achieving a sustained, controlled release of the volatile substance from the foam structure which comprises impregnating a volatile substance in situ into a foam structure by admixing a capped polyoxyethylene polyol having a defined isocyanate functionality of from about 2 to about 8 with water and a non-polar volatile organic compound to obtain a homogenous mixture and curing the resulting foam at ambient conditions.

6. The method as in claim 5 wherein the capped polyol is an isocyanate-capped polyoxyethylene polyol.

7. The method as in claim 5 wherein a surface active agent is added to the reaction mixture.

8. The method as in claim 5 wherein a compound selected from the group consisting of absorptive agents, adsorptive agents, gums, resins, esters, ethers, oxyethylene polymers, and mixtures thereof is added to the reaction mixture.

9. The method as in claim 5 wherein said volatile organic compound is selected from the group comprising organic compounds having:
  a. a vapor pressure greater than about 10 mm of mercury at 160° C.;
  b. a melting point at atmospheric pressure not higher than 200° C.;
  c. a dielectric constant not greater than 30 and preferably less than about 10; and
  d. a specific gravity at 21° C. of between 0.6 and 1.7.

* * * * *